United States Patent [19]

Austin et al.

[11] Patent Number: 5,702,390
[45] Date of Patent: Dec. 30, 1997

[54] BIOPLAR CUTTING AND COAGULATION INSTRUMENT

[75] Inventors: Charles E. Austin; Kenneth R. Dafforn, both of Mason, Ohio; Jay J. McElhenney, Barrington, R.I.

[73] Assignee: Ethicon Endo-Surgery, Inc., Cincinnati, Ohio

[21] Appl. No.: 614,117

[22] Filed: Mar. 12, 1996

[51] Int. Cl.$^6$ .................................................. A61B 17/39
[52] U.S. Cl. .......................... 606/48; 606/41; 606/50
[58] Field of Search ........................ 606/32, 39, 40, 606/41, 45, 48–52, 205, 207

[56] References Cited

U.S. PATENT DOCUMENTS

| | | | |
|---|---|---|---|
| D. 358,887 | 5/1995 | Feinberg | D24/143 |
| 2,068,721 | 1/1937 | Wappler et al. | |
| 4,655,216 | 4/1987 | Tischer | 128/303.17 |
| 4,802,476 | 2/1989 | Noerenberg et al. | 128/303.14 |
| 5,122,137 | 6/1992 | Lennox | 606/40 |
| 5,201,759 | 4/1993 | Ferzli | 606/207 |
| 5,290,287 | 3/1994 | Boebel et al. | 606/51 |
| 5,322,055 | 6/1994 | Davison et al. | 601/2 |
| 5,324,289 | 6/1994 | Eggers | 606/48 |
| 5,330,471 | 7/1994 | Eggers | 606/48 |
| 5,342,359 | 8/1994 | Rydell | 606/51 |
| 5,352,222 | 10/1994 | Rydell | 606/37 |
| 5,403,312 | 4/1995 | Yates et al. | 606/40 |
| 5,431,674 | 7/1995 | Basile et al. | 606/170 |
| 5,443,463 | 8/1995 | Stern et al. | 606/51 |
| 5,445,638 | 8/1995 | Rydell et al. | 606/51 |
| 5,536,267 | 7/1996 | Edwards et al. | 606/39 |

FOREIGN PATENT DOCUMENTS

| | | |
|---|---|---|
| 0 280 798 B1 | 1/1993 | European Pat. Off. |
| 0 623 316 A1 | 9/1994 | European Pat. Off. ........ A61B 17/28 |
| 854366 | 8/1981 | U.S.S.R. |

*Primary Examiner*—Jennifer Bahr
*Assistant Examiner*—Rosiland Kearney
*Attorney, Agent, or Firm*—Bernard Shay

[57] ABSTRACT

A bipolar electrosurgical instrument having a handle, an end effector and an elongated hollow tube. The handle includes first and second grip members. The end effector includes first, second and third electrodes. The first electrode is substantially triangular in shape. The first electrode is adapted to pivot between an open position and a closed position. The first electrode also pivots around its proximal to distal axis and includes a coagulating surface and a cutting edge. The second and third electrodes are arranged substantially parallel to the first electrode when the first electrode is in the closed position. The elongated hollow tube includes a mechanism connecting the handle to the end effector such that movement of the first and second grip members relative to one another causes the first electrode to move relative to the second and third electrodes.

2 Claims, 7 Drawing Sheets

BIOPLAR CUTTING AND COAGULATION INSTRUMENT

FIELD OF THE INVENTION

The present invention relates, in general, to a bipolar electrosurgical instrument for grasping, manipulating and cutting tissue and, more particularly, to a bipolar electrosurgical instrument including an end effector with a rotatable electrode.

BACKGROUND OF THE INVENTION

Bipolar electrosurgical instruments include bipolar shears, bipolar forceps and bipolar cutting forceps. Bipolar shears are generally used to cut tissue and are not generally useful for grasping or manipulating tissue. In bipolar-shears, wherein the tissue between the blades and distal to the cutting point is cauterized as the blades are closed. Bipolar forceps are generally used to grasp, manipulate and cauterize tissue. However, bipolar forceps are not generally useful for cutting tissue. Bipolar forceps are generally used for grasping, manipulating, cutting and coagulating tissue. In most bipolar forceps, a knife or cutting element is disposed between two opposing jaws which grasp tissue and act as electrodes. In conventional bipolar forceps the operator may cauterize the tissue between the jaws prior to cutting the tissue with a knife or other cutting element. Thus, in such bipolar forceps, the region cauterized is generally larger than the region cauterized using bipolar shears.

It would, therefore, be advantageous to design a bipolar electrosurgical instrument wherein the region of cauterization may be limited as in bipolar shears or enlarged as in bipolar forceps. It would further be advantageous to design such an instrument wherein the end effector is adapted to cut tissue either before, during or after cauterizing the tissue. It would further be advantageous to design such and instrument wherein the instrument may be used to grasp and manipulate tissue. Finally, it would be advantageous to design such an instrument for use in endoscopic and other minimally invasive surgical procedures.

SUMMARY OF THE INVENTION

According to one embodiment of the present invention, a bipolar electrosurgical instrument comprises a handle, an end effector and an elongated hollow tube. The handle includes first and second grip members. The end effector includes first, second and third electrodes. The first electrode is substantially triangular in shape and is adapted to pivot relative to the second and third electrodes about a pivot pin at the proximal end of the end effector. The first electrode pivots between an open position and a closed position. The first electrode also pivots around its proximal to distal axis. The first electrode includes at least one coagulating surface and at least one cutting edge. The second and third electrodes are arranged substantially parallel to the first electrode when the first electrode is in the closed position. The elongated hollow tube includes a mechanism connecting the handle to the end effector such that movement of the first and second grip members relative to one another causes the first electrode to move relative to the second and third electrodes.

Further, according to the present invention, the coagulating surface may be one side of the triangular first electrode and the cutting edge may be formed at the intersection of the remaining two sides of the triangular electrode. The coagulating surface may be convex and may include indentations or serrations for grasping tissue. The two sides of the triangular electrode which meet to form the cutting edge may be concave in shape and form additional coagulating surfaces for coagulating tissue after it has been cut.

The second and third electrodes may be electrically isolated from the first electrode and may further be electrically isolated from each other or may be electrically connected at, for example, the proximal end of the end effector. The second and third electrodes may be physically isolated from each other or they may be joined by a central region. The second and third electrodes are arranged such that the cutting edge on the first electro fits between the first and second electrodes when the end effector is in the closed position. The second and third electrodes may include indentations or serrations for griping tissue.

The central region between the second and third electrodes may comprise an electrically insulating material or an electrically conductive material. The central region may include a channel adapted to receive the cutting edge of the first electrode.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
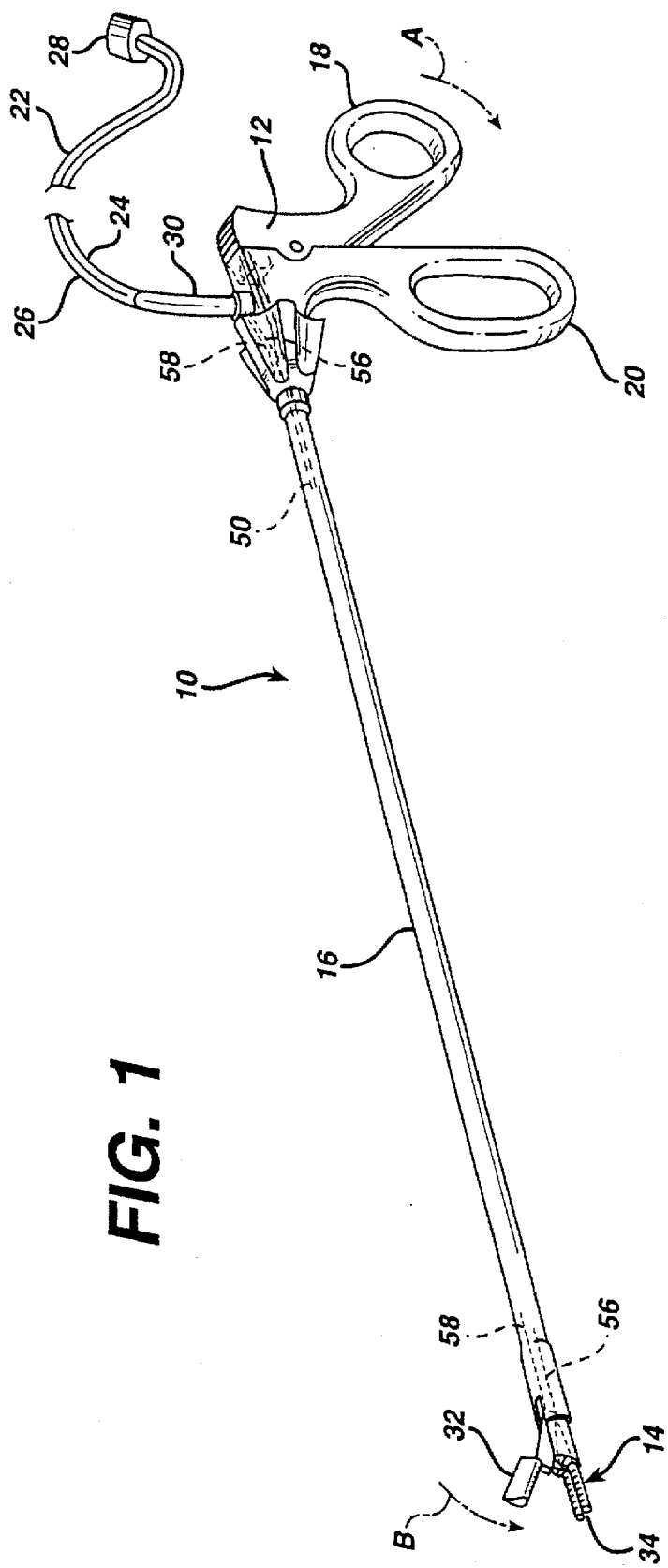
FIG. 1 is a perspective view of a bipolar electrosurgical instrument according to the present invention.

FIG. 1 illustrates a bipolar electrosurgical instrument 10 according to the present invention. In FIG. 1, bipolar electrosurgical instrument 10 comprises a handle 12, an end effector 14 and an elongated hollow tube 16. Handle 12 includes first grip member 18 and second grip member 20. Electrosurgical energy is supplied to instrument 10 through electrical cord 22. Electrical cord 22 includes first wire 24, second wire 26 and bipolar plug 28 which may be connected to a conventional electrosurgical generator (not shown). Electrical cord 22 is connected to electrical connector 30 which is connected to the electrodes in end effector 14 through hollow tube 16 by wires or the like. End effector 14 includes a first jaw member 32 and a second jaw member 34. Movement of grip member 18 in direction A results in closure of end effector 14 by, for example, moving jaw 32 in direction B toward jaw 34.

Figure 2:
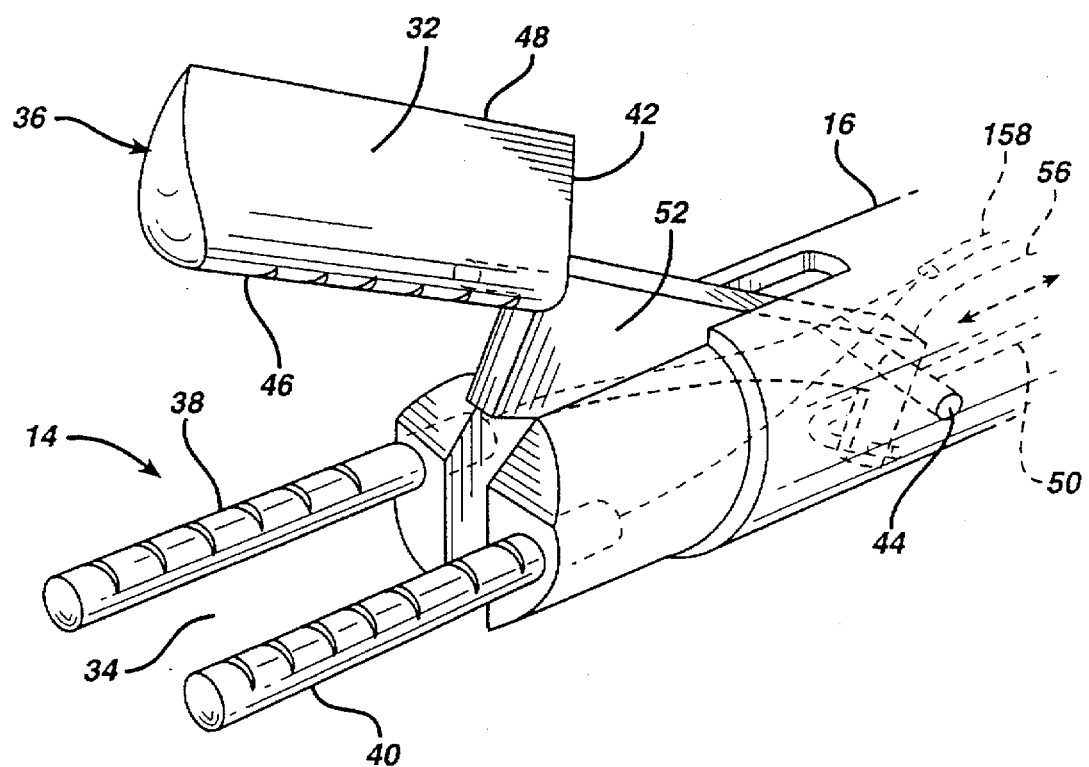
FIG. 2 perspective view of an end effector for a bipolar electrosurgical instrument according to the present invention.
Figure 10:
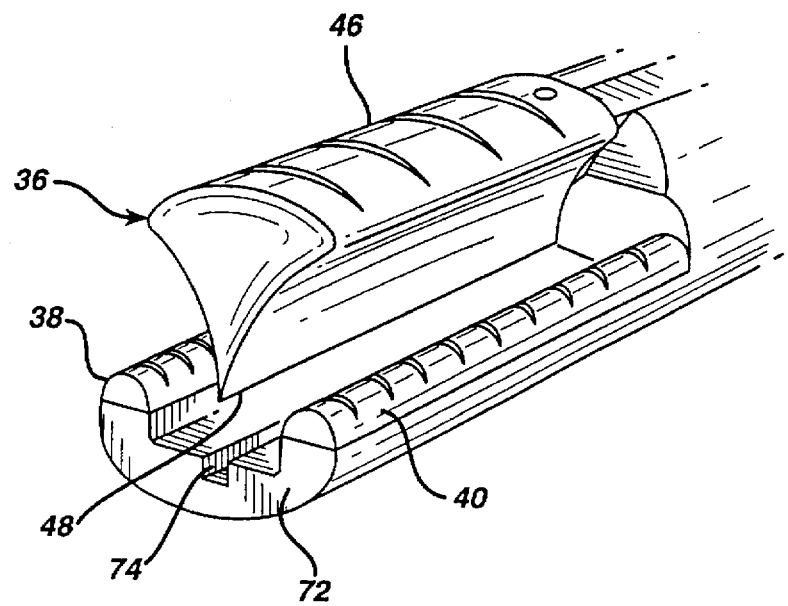
FIG. 10 illustrates an end effector for a bipolar electrosurgical instrument according to the present invention wherein a central supportive region is included between two of the electrodes.

FIG. 2 illustrates an end effector 14 for a bipolar electrosurgical instrument 10 according to the present invention. Jaw 32 includes electrode 36 which may be, for example, a triangular electrode. Jaw 34 includes electrodes 38 and 40 which may be separate as illustrated in FIG. 2 or joined together as illustrated in FIG. 10. Electrode 36 includes coagulating surface 46 and cutting edge 48. In the embodiment of the invention illustrated in FIG. 2, electrode 36 is substantially triangular in shape when viewed from either end. Elongated hollow tube 16 includes a mechanism connecting handle 12 to jaw 32 such that movement of first grip member 18 relative to second grip member 20 causes jaw 32 to move relative to jaw 34. Electrode 36 is adapted to pivot about around its proximal to distal axis and to pivot about insulating pivot pin 44 between a open position as illustrated in FIG. 2 and a closed position as illustrated in FIG. 3.

Electrode 36 is connected to electrical connector 30 by a wire 56 or other suitable conductor. Electrodes 38 and 40 are connected to electrical connector 30 by a wire 158 or other suitable connector. Energy from bipolar plug 28 may be applied to end effector 14 through wires 56 and 58. The application of energy to bipolar plug 28 and, thus, to end effector 14 may be controlled by, for example, using a footswitch (not shown) or other such device.

End effector 14 may be opened and closed by movement of connecting rod 50. Connecting rod 50 is connected to grip member 18 at its proximal end and to lever 52 at its distal end. Movement of connecting rod 50 pivots lever 52 around insulated pivot pin 44. Lever 52 may be insulated to prevent lever 52 from shorting against tube 16. Alternately, hollow tube 16 may be constructed of an insulating material to prevent electrical shorts.

Figure 3:
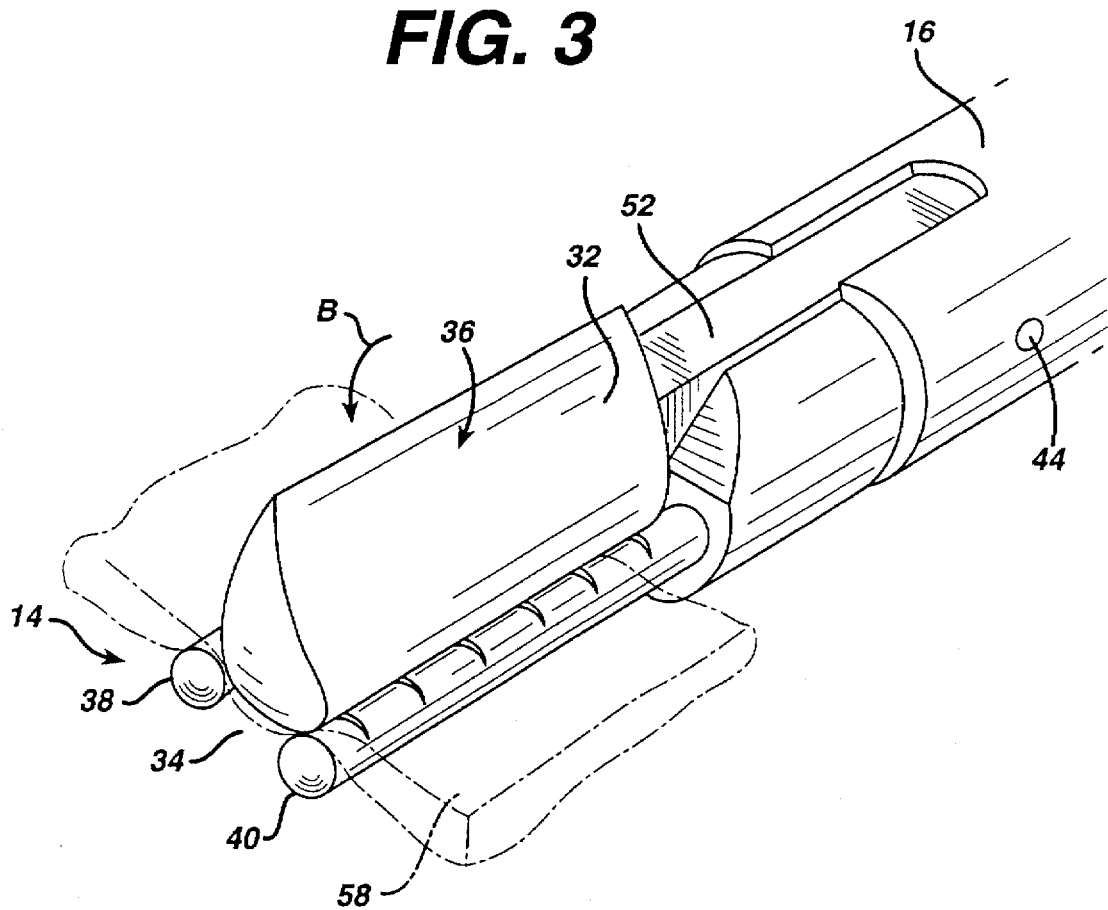
FIG. 3 is a perspective view of an end effector for a bipolar electrosurgical instrument according to the present invention wherein the end effector is in the closed position and the triangular electrode is arranged to coagulate tissue.

FIG. 3 illustrates an end effector for a bipolar electrosurgical instrument 10 according to the present invention wherein jaws 32 and 34 of end effector 14 are in the closed position and Electrode 36 is arranged to coagulate tissue. Electrodes 38 and 40 are substantially parallel to the proximal to distal axis of electrode 36 when electrode 36 is in the closed position as illustrated in FIG. 3. As electrode 36 is closed along B, tissue 58 is grasped between jaw 32 and jaw 34. Tissue 58 grasped between jaws 32 and 34 may be treated by, for example, applying electrosurgical energy between jaw 32 and jaw 34.

Figure 4:
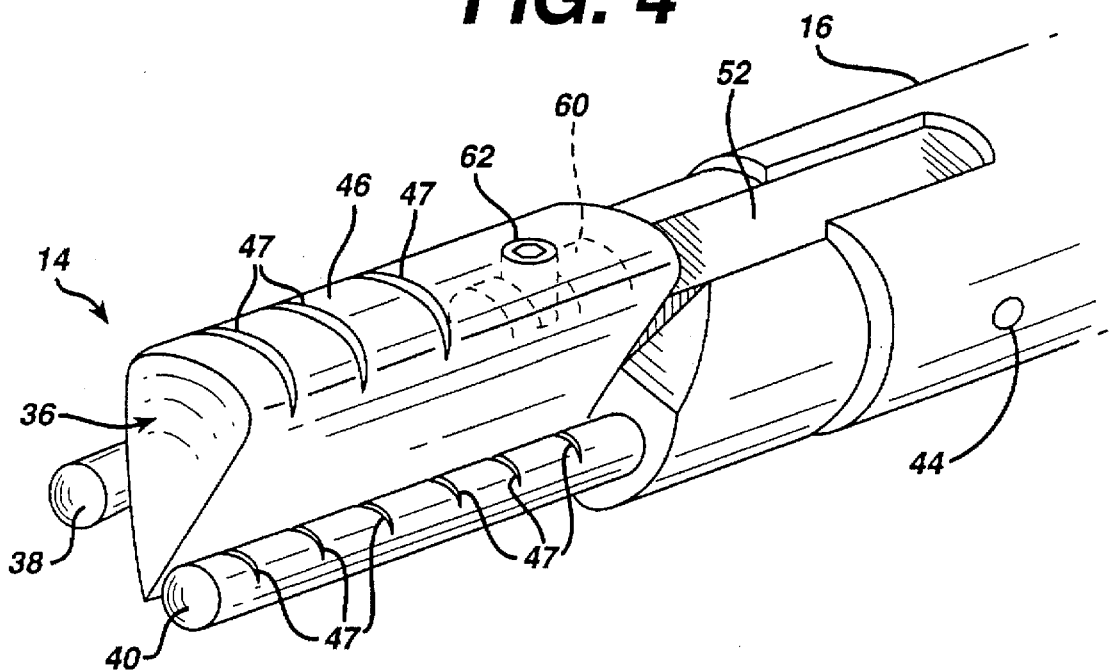
FIG. 4 is a perspective view of an end effector for a bipolar electrosurgical instrument according to the present invention wherein the end effector is in the closed position and the triangular electrode is arranged to cut tissue.

FIG. 4 illustrates an end effector 14 for a bipolar electrosurgical instrument 10 according to the present invention wherein end effector 14 is in the closed position and electrode 36 is arranged to cut tissue. In the embodiment of FIG. 4, electrode 36 is mounted to connector 52 by means of pivot pin 60. Electrode 36 is held in place by set screw 62. As illustrated in FIG. 4, coagulation surface 46 of electrode 36 may include indentations or serrations 47 which assist in grasping and holding tissue. Serrations 47 may also be included on electrodes 38 and 40 to assist in grasping and holding tissue.

Figure 5:
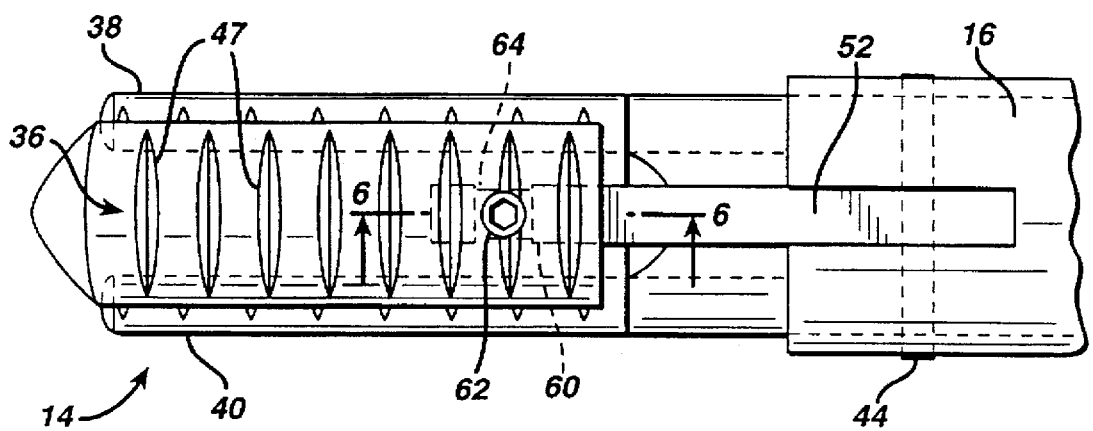
FIG. 5 is a top view of a rotatable attachment mechanism for an end effector for a bipolar electrosurgical instrument according to the present invention.
Figure 6:
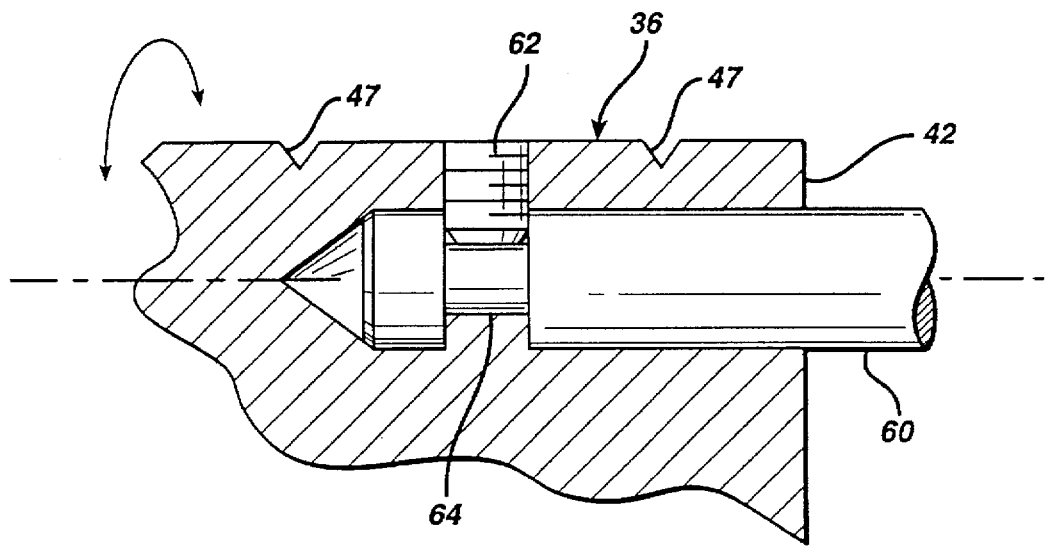
FIG. 6 is a cutaway view along line 6—6 of the end effector illustrated in FIG. 5.

FIG. 5 illustrates a rotatable attachment mechanism for an end effector for a bipolar electrosurgical instrument according to the present invention. FIG. 6 is a cutaway view along 6—6 of the end effector illustrated in FIG. 5. In FIG. 6, set screw 62 rides in channel 64, allowing electrode 36 to pivot 360° around pivot pin 60.

Figure 7:
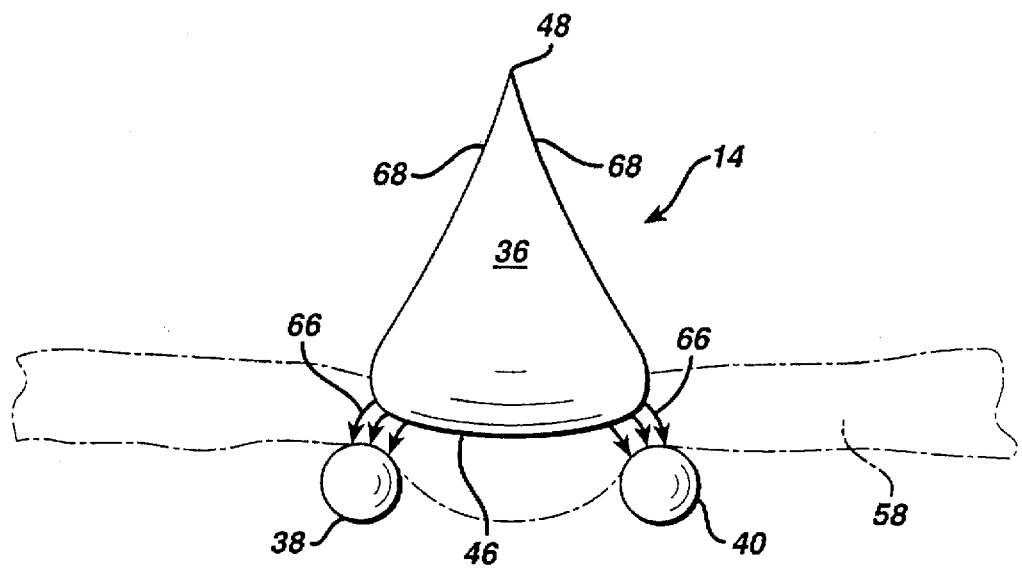
FIG. 7 is end view of an end effector for a bipolar electrosurgical instrument according to the present invention wherein the end effector is in the closed position and the triangular electrode is arranged to coagulate tissue.

FIG. 7 is an end view of an end effector 14 for a bipolar electrosurgical instrument 10 according to the present invention wherein end effector 14 is in the closed position and electrode 36 is arranged to coagulate tissue 58. In FIG. 7, coagulation surface 46 of electrode 36 holds tissue 58 in place against electrodes 38 and 40. Since tissue 58 acts as an electrical conductor, the application of electrosurgical energy to end effector 14 will result in electrical current 66 flowing from electrode 36 to electrodes 38 and 40. The electrical current will act to heat tissue 58, resulting in cauterization and/or desiccation of tissue 58. Thus, in the arrangement illustrated in FIG. 7, end effector 14 may be used to cauterize tissue. End effector 14 may also be used, in the arrangement illustrated in FIG. 4, to grasp and manipulate tissue without applying electrosurgical energy. In the embodiment of FIG. 7, coagulating surface 46 is convex to increase the amount of tissue between coagulating surface 46 and electrodes 38 and 40 increasing the amount of tissue coagulated and enhancing the grasping characteristics of the instrument.

Figure 8:
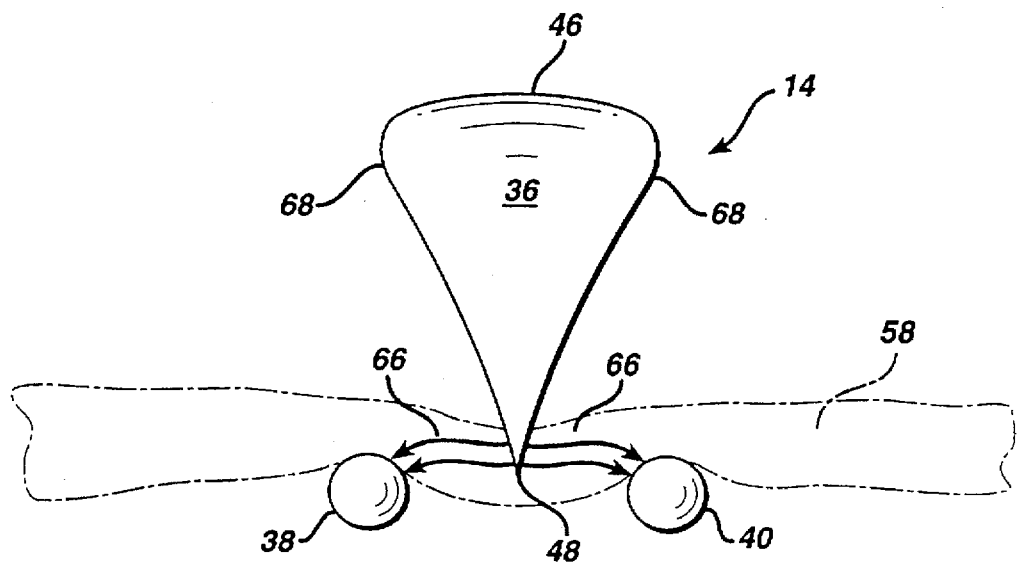
FIG. 8 is an end view of an end effector for a bipolar electrosurgical instrument according to the present invention wherein the end effector is in the partially closed position and the triangular electrode is arranged to cut tissue.

FIG. 8 is an end view of an end effector 14 for a bipolar electrosurgical instrument 10 according to the present invention wherein electrode 36 of end effector 14 is arranged to cut tissue. In FIG. 8, electrosurgical energy is applied to electrode 36 such that, when electrode 36 contacts electrically conductive tissue 58, electrical current 66 will flow from electrode 36 to electrodes 38 and 40. Electrodes 38 and 40 provide a return path for the electrical current from electrode 36. Thus, tissue 58 in the region between electrodes 38 and 40 is cauterized as the end effector is closed and the tissue is cut by cutting edge 48 of electrode 36.

Figure 9:
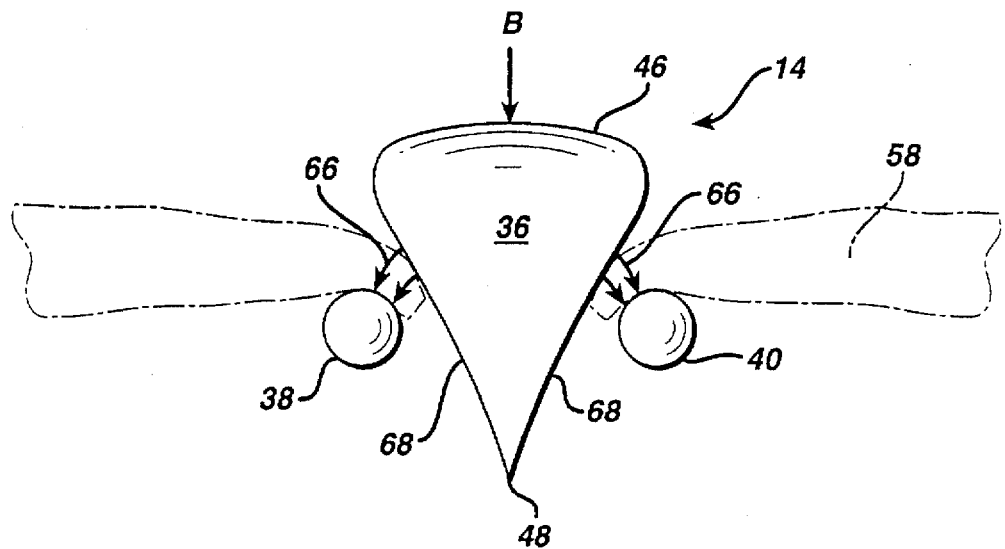
FIG. 9 illustrates an end effector for a bipolar electrosurgical instrument according to the present invention wherein the end effector is in the closed position and the triangular electrode is arranged to cut tissue.

FIG. 9 illustrates an end effector 14 for a bipolar electrosurgical instrument according to the present invention wherein electrode 36 of end effector 14 has cut through tissue 58. As illustrated in FIG. 9, electrical current 66 from electrode 36 continues to flow through tissue 58 for so long as electrosurgical energy is applied and tissue is positioned between electrode 36 and either of electrodes 38 or 40. Thus, even after tissue 58 is cut, the tissue in the region immediately adjacent the cut may be cauterized. Further, as end effector 14 is closed, tissue grasped by end effector 14 will be compressed between jaws 32 and 34, enhancing coagulation of the grasped tissue. In the embodiment of FIG. 9, coagulating surfaces 68 are concave to facilitate the positioning and grasping of tissue between electrode 36 and electrodes 38 and 40. The inclusion of concave coagulating surfaces 68 is also advantageous in that such an arrangement increases the tissue area in contact with the electrodes. Further, the concave sides 68 of electrode 36 provide clearance to facilitate cutting by allowing cutting edge 48 to penetrate well past electrodes 38 and 40.

In the present invention, electrodes 38 and 40 are electrically isolated from electrode 36 and may further be electrically isolated from each other or may be electrically connected at, for example, the proximal end of the end effector. In addition, electrodes 38 and 40 may be physically isolated from each other or they may be joined by a central region as illustrated in FIG. 10. Central region 72 in FIG. 10 may be a nonconductive supporting material, an insulated region of conductive material or an uninsulated region of conductive material. Central region 72 may further include a channel 74 which is adapted to receive cutting edge 48 of electrode 36.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A bipolar electrosurgical instrument, wherein said instrument comprises:

a handle including first and second grip members;

an end effector comprising:

a first triangular shaped electrode pivotable about a first axis between an open position and a closed position, wherein said first electrode is further pivotable around a second axis which is substantially perpendicular to said first axis;

a coagulating surface on a first side of said first electrode;

a cutting edge on a second side of said first electrode;

second and third electrodes arranged substantially perpendicular to said first axis wherein said second and third electrodes are substantially parallel to said second axis when said end effector is in said closed position;

an elongated hollow tube including a mechanism connecting said first grip member to said first electrode.

2. An electrosurgical instrument according to claim 1 wherein said second and third electrodes are joined by an insulting region such that said cutting edge fits between said first and second electrodes and contacts said insulating region when said end effector is in said closed position.

* * * * *